US009474862B2

(12) United States Patent
Walsh

(10) Patent No.: US 9,474,862 B2
(45) Date of Patent: Oct. 25, 2016

(54) WEARABLE MEDICATION ADMINISTRATION DEVICE

(71) Applicant: Jessica Walsh, Upper Brookville, NY (US)

(72) Inventor: Jessica Walsh, Upper Brookville, NY (US)

( * ) Notice: Subject to any disclaimer, the term of this patent is extended or adjusted under 35 U.S.C. 154(b) by 7 days.

(21) Appl. No.: 14/572,013

(22) Filed: Dec. 16, 2014

(65) Prior Publication Data

US 2015/0165126 A1 Jun. 18, 2015

Related U.S. Application Data

(60) Provisional application No. 61/916,314, filed on Dec. 16, 2013.

(51) Int. Cl.
*A61M 5/31* (2006.01)
*A61M 5/32* (2006.01)
*A61M 5/20* (2006.01)

(52) U.S. Cl.
CPC ......... *A61M 5/3129* (2013.01); *A61M 5/2033* (2013.01); *A61M 5/322* (2013.01); *A61M 2005/2026* (2013.01); *A61M 2005/2073* (2013.01); *A61M 2005/3123* (2013.01); *A61M 2205/586* (2013.01); *A61M 2205/6009* (2013.01)

(58) Field of Classification Search
CPC .............. A61M 5/3129; A61M 5/322; A61M 5/2033; A61M 5/002; A61M 5/3202; A61M 2005/206; A61M 2005/312; A61M 25/002
See application file for complete search history.

(56) References Cited

U.S. PATENT DOCUMENTS

| 3,093,242 | A | * | 6/1963 | Huyck | A61B 19/026 106/31.16 |
|---|---|---|---|---|---|
| 3,910,260 | A | | 10/1975 | Sarnoff et al. | |
| 3,939,833 | A | * | 2/1976 | Hansson | A61M 5/31511 604/202 |
| 3,941,130 | A | | 3/1976 | Tibbs | |
| 4,004,577 | A | | 1/1977 | Sarnoff | |
| 4,178,928 | A | * | 12/1979 | Tischlinger | A61M 5/2033 604/139 |

(Continued)

FOREIGN PATENT DOCUMENTS

| WO | 98/13077 A2 | 4/1998 |
|---|---|---|
| WO | 2008/005315 A2 | 1/2008 |

(Continued)

OTHER PUBLICATIONS

International Search Report dated Mar. 16, 2015 issued in PCT/US2013/070438.

*Primary Examiner* — Laura Bouchelle
(74) *Attorney, Agent, or Firm* — Greenberg Traurig, LLP

(57) ABSTRACT

A medication administration device is provided. The device has a flexible tube having an administration end, an activation end and a lumen between the ends. An administration assembly is attached to the administration end. An activation assembly is attached to the activation end. A syringe is disposed within the lumen. The syringe contains the medication and has a first end and an opposite second end. A plunger is disposed within the lumen and operatively connected to the first end of the syringe. A rupturable seal is provided to the second end of the syringe, which end is approximate to the administration end. The activation assembly activates the plunger to break the rupturable seal to establish a fluid communication between the second end of the syringe and the administration assembly. Accordingly, transportation of the medication from the syringe to the medication administration assembly through the medication administration end is allowed.

9 Claims, 13 Drawing Sheets

(56) References Cited

U.S. PATENT DOCUMENTS

| | | | |
|---|---|---|---|
| 4,261,358 A | | 4/1981 | Vargas et al. |
| 4,525,164 A | | 6/1985 | Loeb et al. |
| 4,685,902 A | * | 8/1987 | Edwards ........... A61M 5/14244 604/151 |
| 4,689,042 A | | 8/1987 | Sarnoff et al. |
| 4,755,169 A | | 7/1988 | Sarnoff et al. |
| 4,768,688 A | * | 9/1988 | Harrigan ................ A44C 5/003 206/37 |
| 4,795,433 A | | 1/1989 | Sarnoff |
| 4,865,590 A | | 9/1989 | Marmar |
| 4,921,277 A | * | 5/1990 | McDonough ............. G09F 3/00 283/100 |
| 5,064,413 A | * | 11/1991 | McKinnon ............... A61M 5/30 604/143 |
| 5,085,642 A | | 2/1992 | Sarnoff et al. |
| 5,092,843 A | | 3/1992 | Monroe et al. |
| 5,102,393 A | | 4/1992 | Sarnoff et al. |
| 5,135,479 A | * | 8/1992 | Sibalis .................. A61M 37/00 604/20 |
| 5,217,143 A | * | 6/1993 | Aitken ................. A44C 15/002 206/823 |
| 5,267,963 A | | 12/1993 | Bachynsky |
| 5,536,249 A | | 7/1996 | Castellano et al. |
| 6,149,626 A | | 11/2000 | Bachynsky et al. |
| 6,270,479 B1 | | 8/2001 | Bergens et al. |
| 6,371,939 B2 | | 4/2002 | Bergens et al. |
| 6,800,070 B2 | * | 10/2004 | Mazidji ................. A44C 5/0023 604/147 |
| 6,926,699 B2 | * | 8/2005 | Stone ................. A61M 25/0084 604/218 |
| 8,109,912 B2 | * | 2/2012 | Alferness .......... A61M 5/14248 604/181 |
| 2005/0273054 A1 | | 12/2005 | Asch |
| 2013/0079747 A1 | | 3/2013 | Gross et al. |

FOREIGN PATENT DOCUMENTS

| | | |
|---|---|---|
| WO | 2009/070605 A1 | 6/2009 |
| WO | 2010/089589 A1 | 8/2010 |
| WO | 2012/090186 A1 | 7/2012 |
| WO | 2013/019939 A2 | 2/2013 |
| WO | 2013/034986 A2 | 3/2013 |
| WO | 2014/063112 A1 | 4/2014 |

* cited by examiner

WEARABLE MEDICATION ADMINISTRATION DEVICE

This application claims the benefit of priority to U.S. Provisional Application Ser. No. 61/916,314, filed on Dec. 16, 2013, which is incorporated by reference into the present application.

FIELD OF THE INVENTION

The described invention relates to a wearable device for administering a medication into a subject in need thereof.

BACKGROUND OF THE INVENTION

Devices have been used to administer medications under emergency conditions, such as, for example, administering epinephrine to counteract the effects of a severe allergic reaction. Devices have also been described for use in administering medications to treat disease, such as, for example, anti-arrhythmic medications and selective thrombolytic agents during a heart attack.

Automatic medication administration devices offer an alternative to manually operated syringes for administering therapeutic agents into subjects in need thereof, or allowing subjects in need thereof to self-administer medications. Frequently, automatic medication administration devices administer medication to the subject via injection. Examples of automatic medication injection devices may be found, for example, in U.S. Pat. Nos. 3,910,260; 4,004,577; 4,689,042; 4,755,169; 4,795,433; 3,941,130; 4,261,358; 5,085,642; 5,092,843; 5,102,393; 5,267,963; 6,149,626; 6,270,479; 6,371,939; and PCT publication WO/2008/005315.

Current automatic medication administration devices are frequently cumbersome and may not be readily accessible, or easily carried by the user. In particular, due to the bulk of the current automatic medication administration devices, the devices tend to be carried in the subject's bag, or back pack, or purse, or car, not on the subject's person. In addition, the currently available automatic medication administration devices have a number of problems in form, function, and appeal. These problems can contribute to incorrect use, misuse, not carrying the unit as prescribed (non-compliance), and can result in an adverse outcome including death. By way of example, anaphylaxis is a severe medical emergency that if not treated quickly and appropriately can be fatal. It occurs unexpectedly and may progress rapidly in patients of all ages, but most often in the young and otherwise healthy. One common cause of anaphylaxis is food allergy, especially to peanuts, which is increasing in prevalence. Other causes exist, such as, for example, other food allergens, adverse reactions to medications, or adverse reactions to insect bites or stings. Rapid diagnosis is essential and immediate injection of intramuscular epinephrine is the treatment of choice, the response to which is often dramatic and potentially life saving. The early injection of epinephrine is the most important factor in anaphylaxis outcome. People who survive near fatal anaphylactic reactions receive intramuscular injections promptly while those who die do not.

What is needed therefore is a portable, wearable, accessible, and easy to use device for the rapid administration of medication to a subject in need thereof.

SUMMARY OF THE INVENTION

The present invention provides a medication administration device that can be worn on the subject's person, or attached to the subject's person, clothing, or equipment.

In one aspect, the medication administration device includes a flexible tube that includes a medication administration end, an activation end and a lumen between the medication administration end and the activation end. The device further includes a medication administration assembly attached to the medication administration end and an activation assembly attached to the activation end. The device further includes a syringe disposed within the lumen. The syringe contains the medication and has a first end and an opposite second end. A plunger is disposed within the lumen and operatively connected to the first end of the syringe. A rupturable seal is provided to the second end of the syringe. The second end of the syringe is approximate to the medication administration end. The activation assembly is configured to activate the plunger and break the rupturable seal, such that a fluid communication is established between the second end of the syringe and the medication administration assembly to allow transportation of the medication from the syringe to the medication administration assembly through the medication administration end.

In one aspect, the medication administration end and the activation end of the flexible tube are configured to operatively approach each other to form a partial loop of the flexible tube.

In a further aspect, a cover member is provided, into which the medication administration end and the activation end of the flexible tube, the medication administration assembly, and the activation assembly are received to form a closed loop.

In one aspect, the medication administration assembly includes a needle in fluid communication with the medication administration end. The needle has a first position where the needle is retracted within the medication administration assembly, and a second position where the needle extends out of the medication administration assembly, thereby allowing insertion of the needle into the subject to administer the medication to the subject. For example, the needle moves to the second position upon the activation of the plunger and the breakage of the rupturable seal. For example, a secondary rupturable seal is provided to an end of the administration assembly, the end being distal to the medication administration end of the flexible tube, and the needle punctures the second rupturable seal when the needle is at the second position. For example, the needle is spring-biased within the medication administration assembly.

In one aspect, the plunger forms an air-tight seal within the syringe, such that when the plunger is activated by the activation assembly, a pressure is applied to the medication within the syringe, the pressure being sufficient to break the rupturable seal.

In one aspect, the activation assembly includes a force generator for generating a force to move the plunger within the lumen, in a direction from the activation end to the medication administration end of the flexible tube, and an activator operatively connected to the force generator to control the force generator. For example, the force generator includes a cartridge containing pressurized fluid, and the activator includes a button for controlling the release of the pressurized fluid. For example, a cap is provided for covering the button, the cap being pivotably mounted to the activator through a hinge. For example, one or more vents are provided to the flexible tube, through which the pressurized fluid is released from the lumen. For example, the force generator includes a spring.

In one aspect, the plunger forms an air-tight seal within the lumen.

In one aspect, at least one tag is removably attached to the flexible tube, the tag being representative of information related to at least one of a medical condition of the subject and the medication.

In one aspect, the syringe is flexible. In one aspect, the plunger is flexible.

In one aspect, the activation assembly has button that once depressed, causes the transmission of a force into the flexible tube, which causes the administration of the medication to the subject through the administration assembly. In a further aspect, the force moves the plunger of the syringe. In a further aspect, movement of the plunger ruptures the seal of the second end of the syringe.

In one aspect, the medication administration assembly has a retracted hypodermic needle, which de-retracts and administers medication to the subject once the button on the activation assembly is depressed. In a further aspect, rupture of the seal of the second end of the syringe and movement of medication into the medication administration assembly de-retracts the hypodermic needle and administers medication to the subject.

In an alternate aspect, the medication administration assembly administers medication to the subject when the medication administration device is activated without the use of a hypodermic needle, once the button on the activation assembly is depressed. In a further aspect, rupture of the seal of the second end of the syringe and movement of medication into the medication administration assembly administers medication to the subject.

In an alternate aspect, the medication administration device of the present invention is formed into a closed bracelet or loop by inserting the activation end and the medication administration end into a clasp.

In an alternate aspect, the medication administration device of the present invention is formed into an open bracelet or loop by bending the medication administration device around the site where the subject desires to wear or attach the medication administration device.

In an alternate aspect, the medication administration device of the present invention is customizable.

In an alternate aspect, the medication administration device of the present invention is identifies the medication that is contained within the flexible tube.

In one aspect, the medication administration device of the present invention delivers at least one dose of medication to a subject in need thereof. In another aspect, the subject can select the dose of medication to be administered.

In one aspect, the medication administration device of the present invention is disposable.

In one aspect, the present invention provides a method of administering medication to a subject in need thereof using a medication administration device of the present invention.

DETAILED DESCRIPTION

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention.

The following description of example embodiments is, therefore, not to be taken in a limited sense, and the scope of the present invention is defined by the appended claims.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

In one embodiment, the present invention provides a wearable device for administering a medication into a subject in need thereof.

Figure 1:
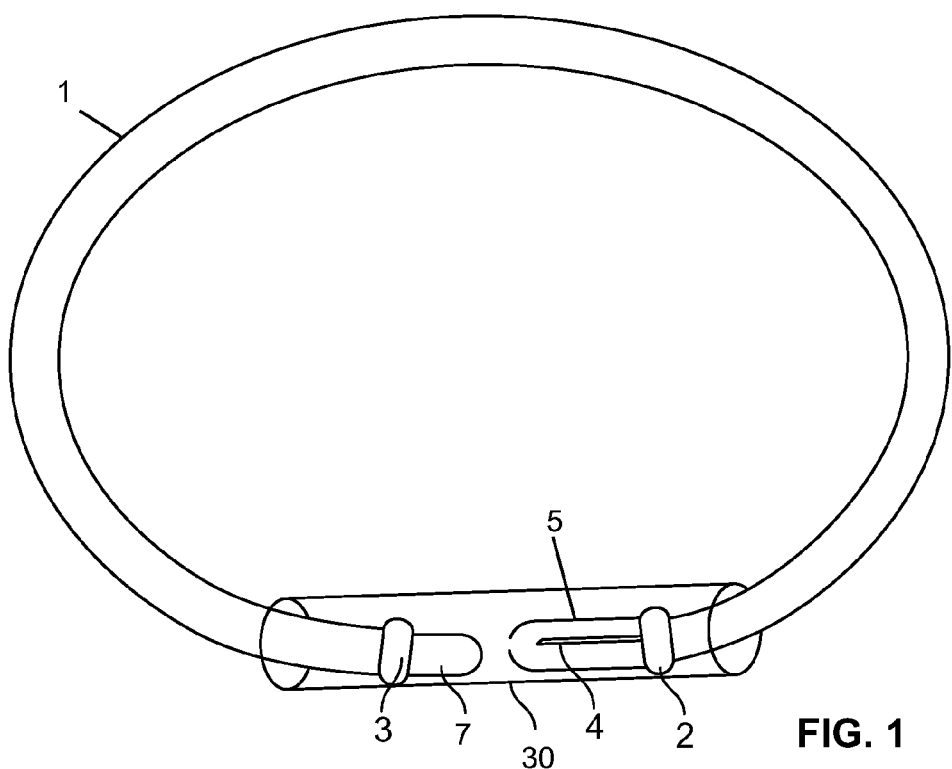
FIG. 1 shows one embodiment of the medication administration device of the present invention in a configuration that secures the automatic medication administration device of the present invention to a subject's person by forming a closed ring (also referred to herein as a "closed configuration").

FIG. 1 shows an exterior view of one embodiment of a medication administration device in accordance with one embodiment of the present invention. In the embodiment shown, the device comprises a flexible tube 1, having medication administration end 2 and an activation end 3. The flexible tube 1 can be filled with a medication. In the embodiment shown, the medication administration end has a medication administration assembly 5 attached comprising a retractable hypodermic needle 4. The activation end has an activation assembly 7 that de-retracts the hypodermic needle 4 and administers the medication to a subject in need thereof. The device is shown with the medication administration end and the activation end (with assemblies attached) inserted into a cover member or clasp 30.

Figure 2:
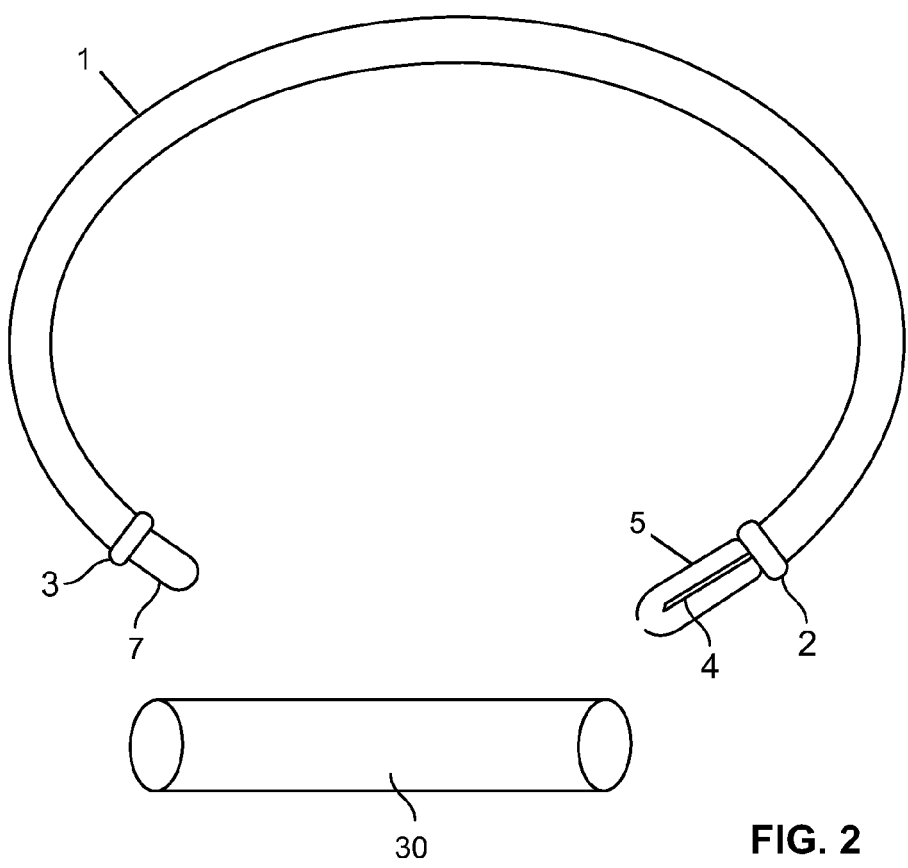
FIG. 2 shows one embodiment of the medication administration device of the present invention in an open configuration that allows the automatic medication administration device of the present invention to be removed from a subject's person.

In one embodiment, insertion of the medication administration end and the activation ends into the clasp 30 forms a loop that allows a subject to secure the device to the subject's person. In one embodiment, insertion of the medication administration end and the activation ends into the clasp prevents the device from administering medication. FIG. 2 shows the embodiment of the medication administration device shown in FIG. 1 with the cover member or clasp 30 removed.

Figure 3:
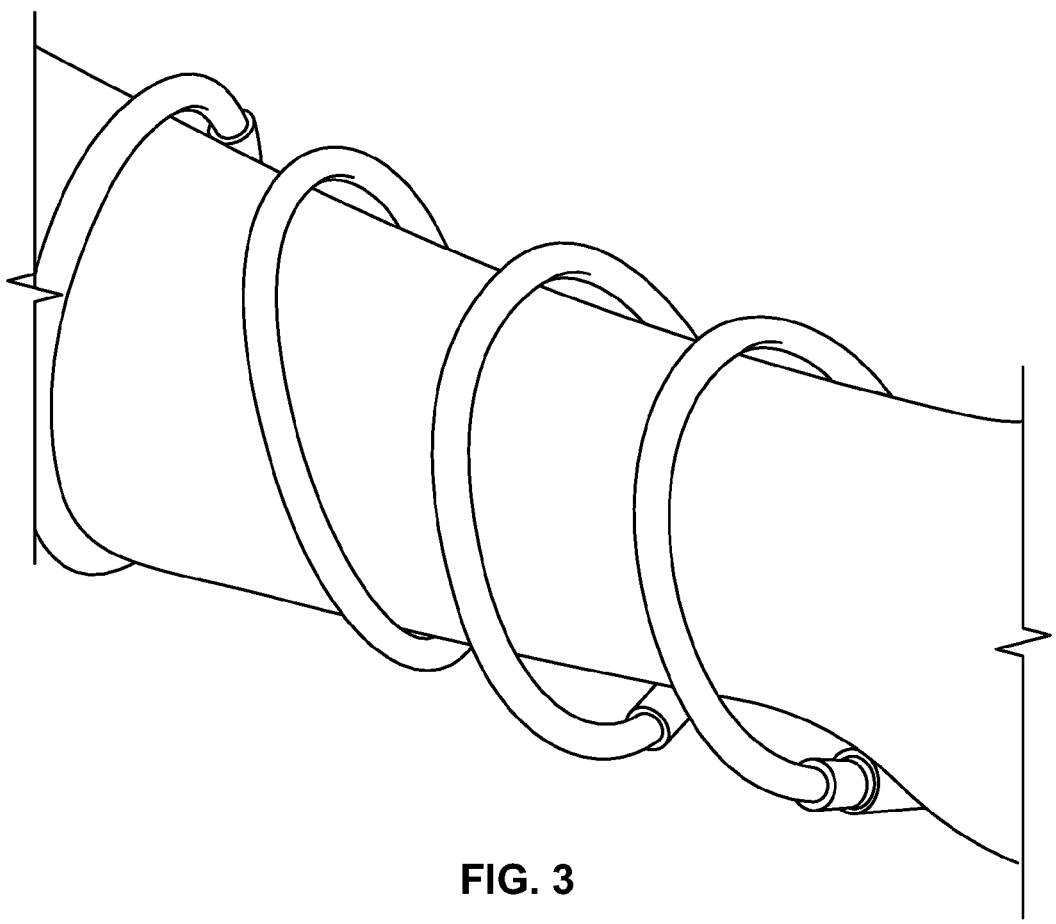
FIG. 3 shows a subject wearing multiple devices of the embodiment shown in FIG. 1.

FIG. 3 shows an alternate exterior view of a medication administration device in accordance with one embodiment of the present invention. In this figure, a subject is shown wearing multiple devices.

Figure 4:
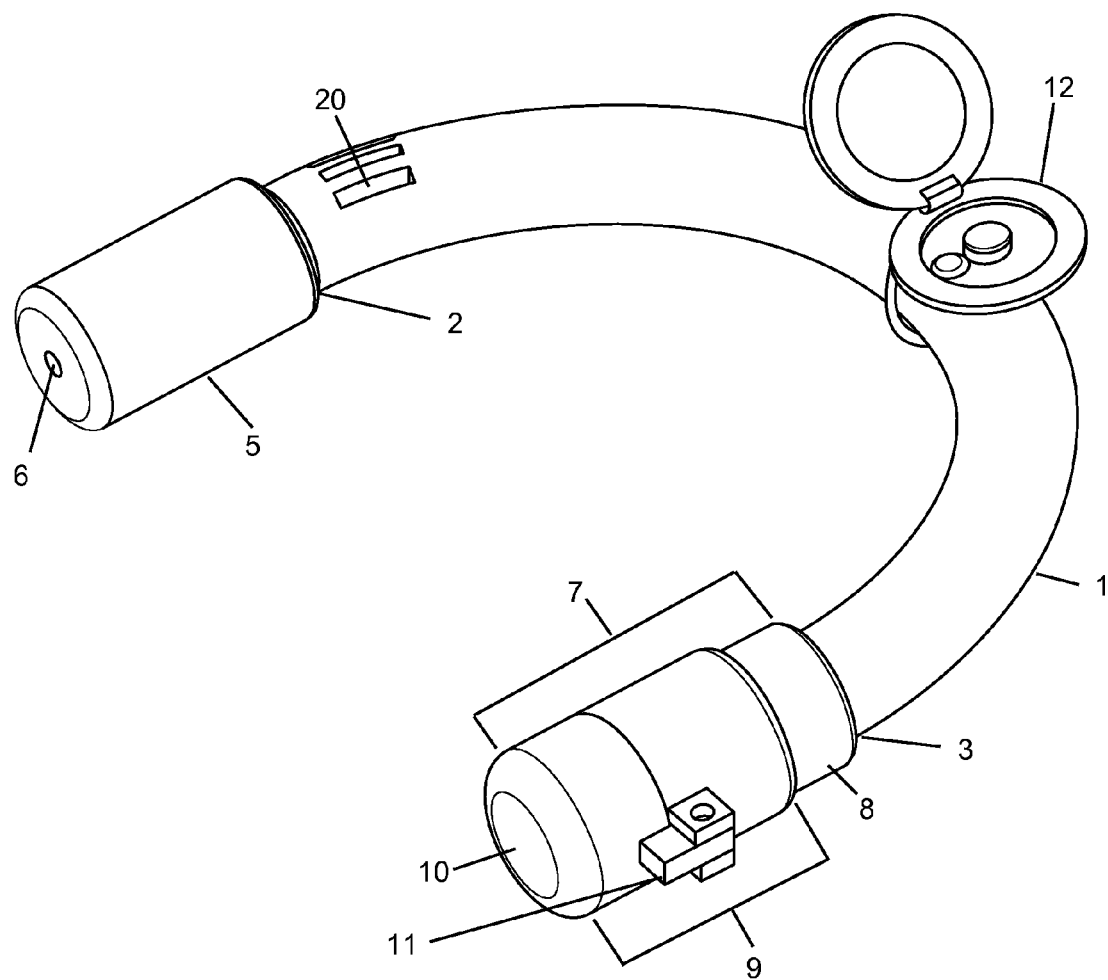
FIG. 4 shows an alternate embodiment of the medication administration device of the present invention that forms an open bracelet, with the tag shown in FIG. 16 attached.

FIG. 4 shows an exterior view of one embodiment of a medication administration device in accordance with an alternate embodiment of the present invention. In the embodiment shown, the device comprises a flexible tube 1, having medication administration end 2 and an activation end 3. In the embodiment shown, the flexible tube 1 has vents 20 at the medication administration end 2. The vents 20 may be further configured to prevent contamination of the medication administration device. In alternate embodiments, vents 20 are absent. Attached to the medication administration end 2 is a medication administration assembly 5. The medication administration assembly 5 has a sealed end 6 that ruptures when the medication administration device is activated allowing the medication to be administered. In one embodiment, the sealed end 6 prevents contamination of the medication administration device. Attached to the activation end 3 is an activation assembly 7. In the embodiment shown, the activation assembly 7 comprises a deployment assembly 8 that transmits a force to medication contained within flexible tube 1. Attached to the deployment assembly 8 is an activator 9, which is opened by moving the top 10 about the hinge 11. In the embodiment shown, opening the activator 9 exposes the mechanism to activate the medication administration device. A pendant or tag 12 is shown attached to flexible tube 1.

Figure 5:
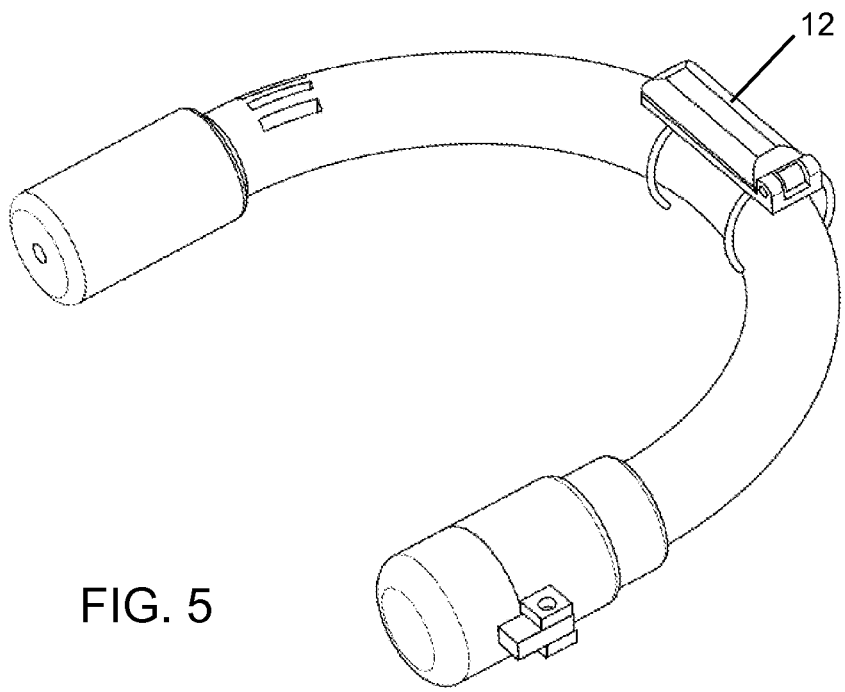
FIG. 5 shows an alternate embodiment of the medication administration device of the present invention that forms an open bracelet, with the tag shown in FIG. 19 attached.

FIG. 5 shows an alternate embodiment of a pendant or tag 12 attached to flexible tube 1.

Figure 6:
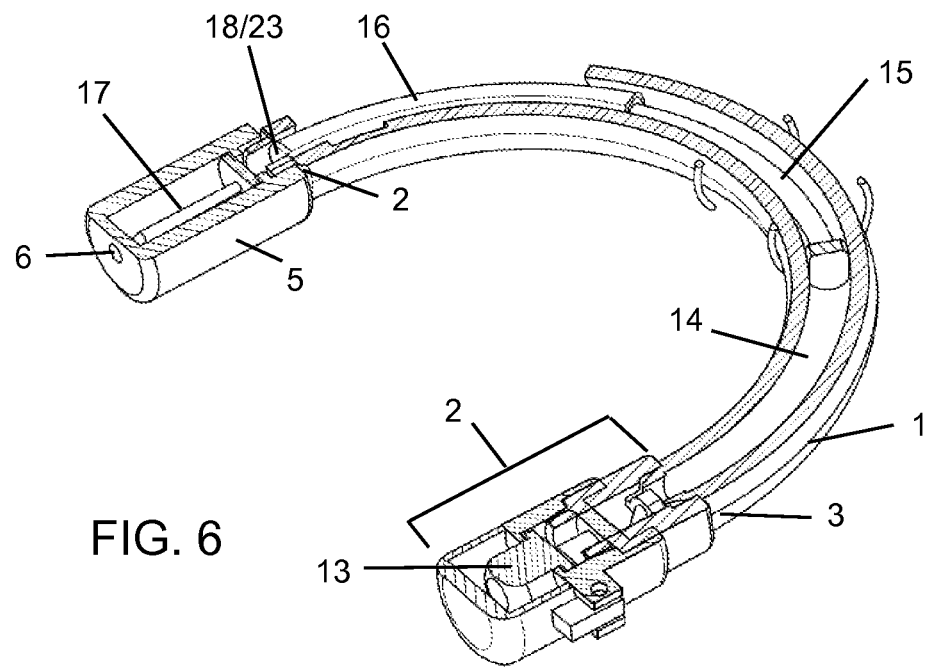
FIG. 6 shows a cut away view of an alternate embodiment of the medication administration device of the present invention that forms an open bracelet.

FIG. 6 shows a cut away view of one embodiment of the medication administration device shown in FIG. 5. Referring to FIG. 6, the activation assembly 7, within the assembly is a button 13 that can be depressed by the subject or user. Flexible tube 1 has a lumen 14 that contains syringe 16, with plunger 15 at the first end of the syringe, and a rupturable seal 18 at the second end 23 of syringe 16. In the embodiment shown, the second end 23 of syringe 16 is immediately adjacent to the medication administration end 2. In the embodiment shown, the medication administration assembly 5 has a retracted hypodermic needle 17.

In certain embodiments, syringe 16 is flexible. In certain embodiments, plunger 15 is flexible. In certain embodiments, plunger 15 forms an airtight seal in lumen 14. In certain embodiments, plunger 15 forms an airtight seal in syringe 16. In operation, the activation assembly 7 is configured to activate the plunger 15 and break the rupturable seal 18, such that a fluid communication is established between the second end 23 of the syringe 16 and the medication administration assembly 5 to allow transportation of the medication from the syringe 16 to the medication administration assembly 5 through the medication administration end 2.

Figure 7:
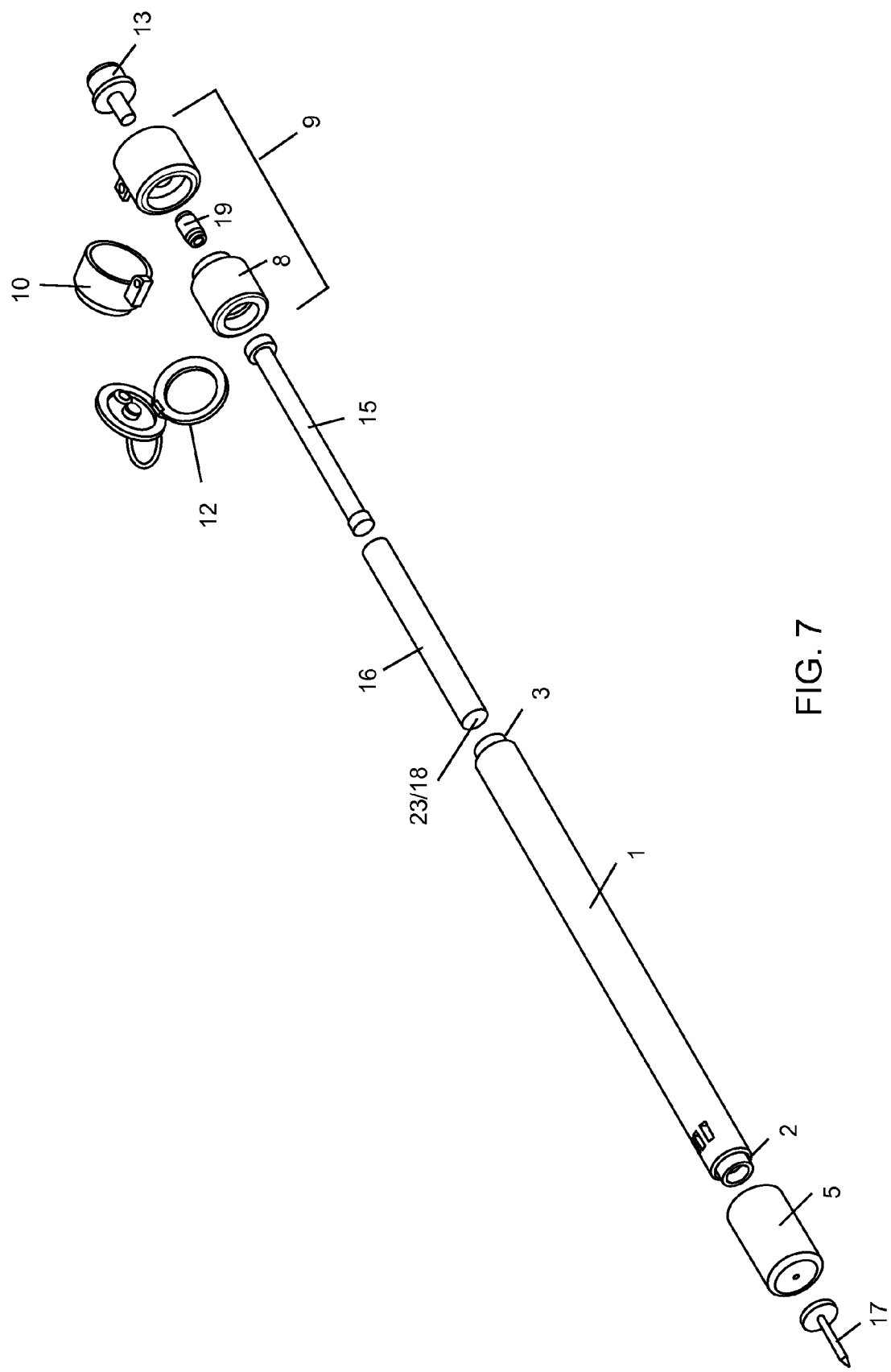
FIG. 7 shows an exploded view of one embodiment of the medication administration device of the present invention that forms an open bracelet.

FIG. 7 shows an alternate view of the embodiment of the medication administration device shown in FIG. 5, with the components laid out. Referring to FIG. 7, a force generator 19 in the form of a gas cartridge is shown. The gas cartridge contains therein pressurized medium, for example, gas. In the embodiment shown, gas cartridge 19 is located between deployment assembly 8 and activator 9. In the embodiment shown, gas cartridge 19 provides force to plunger 15 to administer the medication. In the embodiment shown, the released gas may exit the device through vents 20.

While the embodiment described in FIG. 7 depicts the force generator in the form of a gas cartridge to supply force, one of ordinary skill in the art can readily appreciate other means to generate force via activation assembly 7. For example, the force may be applied mechanically, via means including but not limited to a plunger, a spring, pressure, vacuum, magnet, gas cartridge, or combinations thereof. Alternatively, the force may be applied electromechanically.

Figure 8:
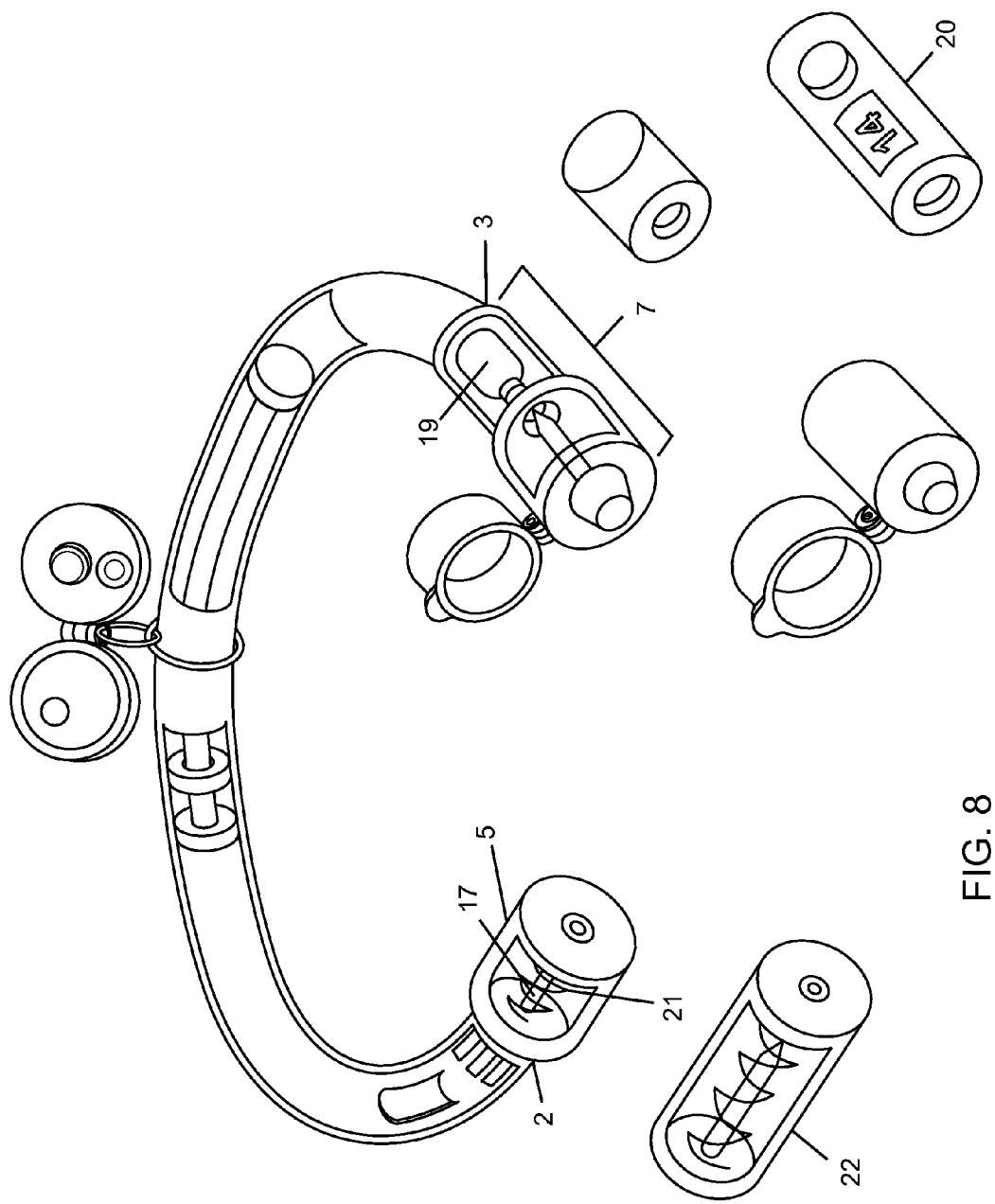
FIG. 8 shows an alternate embodiment of the medication administration device of the present invention that forms an open bracelet, with the tag shown in FIG. 16 attached. A variety of first and second ends are also shown.

FIG. 8 shows a variety of activation assemblies. Shown attached to the activation end 3 is an activation assembly 7, wherein gas cartridge 19 is located between deployment assembly 8 and activator 9. One of ordinary skill in the art can readily appreciate that gas cartridge 19 can be replaced with a spring, or other means to apply force. For example, an alternative deployment assembly 20 is shown, that contains a mechanism to regulate the amount of medication administered.

FIG. 8 shows a variety of administration assemblies that employ hypodermic needles. Shown attached to the medication administration end 2 is a medication administration assembly 5, wherein hypodermic needle 17 is retracted and held in place by a spring 21. One of ordinary skill in the art can readily appreciate that hypodermic needle 17 can be replaced with a hypodermic needle of a different length, or spring 21 can be replaced with a spring of a different tension. For example, an alternative medication administration assembly 22 is also shown, that contains a hypodermic needle 17 of a different length.

One of ordinary skill in the art can readily appreciate that medication may be administered to the subject without the use of a hypodermic needle. In these embodiments, medication administration assembly 5 would not contain a hypodermic needle. Instead, medication administration assembly 5 would contain a mechanism that administers medication in another way.

The Medication Administration Assembly.

In one embodiment, the medication administration assembly 5 is attached to the medication administration end 2 of flexible tube 1. The medication administration assembly 5 may be connected to the medication administration end 2 of flexible tube 1 of the medication administration device of the present invention by any suitable mechanism. Such mechanisms include, for example, the standardized system of small-scale fluid fittings used for making leak-free connections between a male-taper fitting and its mating female part on medical and laboratory instruments, including hypodermic syringe tips and needles, known as the Luer lock. The medication administration assembly 5 may be attached to the medication administration end 2 of flexible tube 1 by any mechanism that complies with ISO 594 standards. Alternatively, the medication administration assembly 5 may be attached to the medication administration end 2 of flexible tube 1 by any mechanism that complies with DIN and EN standards 1707:1996 and 20594-1:1993.

In one embodiment, the medication administration assembly 5 is attached to the medication administration end 2 of flexible tube 1 according to the methods described in EP927054 B1.

In certain embodiments, the medication administration assembly 5 comprises a retractable hypodermic needle 17 within a sealed assembly that is attached to the administration end 2 of the flexible tube 1. The hypodermic needle 17 enables the medication that is stored within the flexible tube to be administered to the subject. The medication may be administered intravenously, or, alternatively, subcutaneously, or, alternatively, intramuscularly. An example of an administration assembly comprising a retractable hypodermic needle within a sealed assembly is shown in FIG. 6.

One of ordinary skill in the art can readily select the type of hypodermic needle that may be used. The choice of needle may be dictated by several factors, including, for example, the site where a particular medication may be administered to a subject, the nature of the medication, the volume of medication that may be administered, the age of the subject, the species of the subject, the type of medication to be administered, the route of administration, and the like.

An alternate needle suitable for use in the automatic medication administration device of the present invention is disclosed in EP927054 B1.

In one embodiment, the needle used in the automatic medication administration device of the present invention is ½ inch long.

In one embodiment, the needle used in the automatic medication administration device of the present invention is ⅝ inch long.

In one embodiment, the needle used in the automatic medication administration device of the present invention is a 23-gauge needle.

Figure 10:
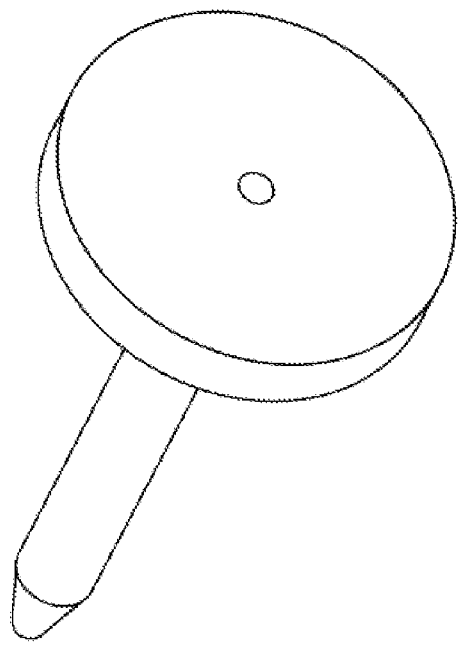
FIG. 10 shows a hypodermic needle of a second length removed from one embodiment of the administration assembly.
Figure 9:
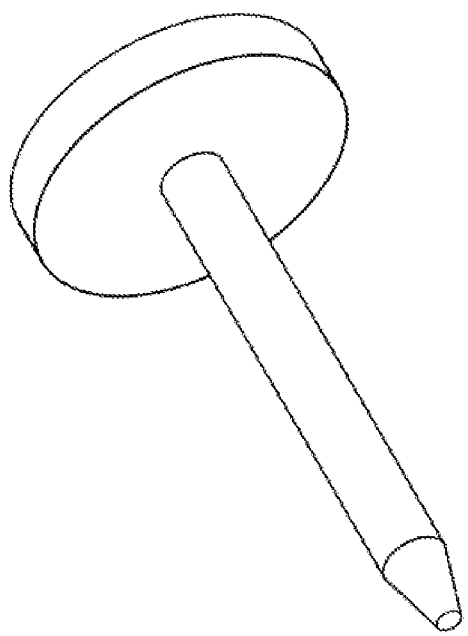
FIG. 9 shows a hypodermic needle of a first length removed from one embodiment of the administration assembly.

FIGS. 9 and 10 show examples of hypodermic needles adapted for use in the automatic medication administration device of the present invention.

In one embodiment, the hypodermic needle is manually exposed or de-retracted by the subject. In alternate embodiments, the medication administration assembly may de-retract the hypodermic needle automatically or mechanically under certain conditions, such as, for example, when the medication administration device of the present invention is placed at a site on the subject.

In one embodiment, the hypodermic needle 17 is moveable from a needle storage position, retracted position or first position, in which the hypodermic needle is retracted within the medication administration assembly to a medication delivering position, de-retracted position or second position in which the needle extends out of the medication administration assembly 5.

Using the device described in FIG. 6 as an example, and without intending to be limited thereby, depression of button 13 activates the device, releasing a force, and the force is transmitted from the deployment assembly 8 into the lumen 14 of flexible tube 1. In the embodiment shown, the force is provided by button 13 causing gas cartridge 19 to release some, or all of its contents (see FIG. 8). The force presses against plunger 15, and causes the second end 23 of syringe 16 to rupture. The rupture of the second end 23 of syringe 16 de-retracts hypodermic needle 17 and ruptures sealed end 6.

In one embodiment, hypodermic needle 17 is moved into the medication delivering position by removing the medication administration assembly 5 from clasp 6. One of ordinary skill in the art may readily appreciate the mechanisms by which the needle may move from a storage position to a medication delivering position. One such mechanism is disclosed in PCT publication WO/2012/090186 A1.

Alternatively, the hypodermic needle may be covered with a sheath. The sheath may be removed to enable the medication to be administered. One of ordinary skill in the art may readily appreciate the mechanisms by which the needle protected by a sheath. One such mechanism is disclosed in PCT publication WO/2010/089589 A1.

In certain embodiments, the medication administration assembly 5 comprises an assembly that is capable of administering medication without a hypodermic needle (referred to herein as a needle-free administration). The medication may be administered intravenously, or, alternatively, subcutaneously, or, alternatively, intramuscularly. One of ordinary skill in the art can readily select a needle-free administration device that can be adapted for use in the present invention. The choice of needle-free administration device may be dictated by several factors, including, for example, the site where a particular medication may be administered to a subject, the nature of the medication, the volume of medication that may be administered, the age of the subject, the species of the subject, the type of medication to be administered, the route of administration, and the like.

For example, WO2013019939A2 describes a needle-free administration device that can be adapted for use in the present invention.

In another example, WO2014063112A1 describes a needle-free administration device that can be adapted for use in the present invention.

In another example, EP2217310A4 describes a needle-free administration device that can be adapted for use in the present invention.

In one embodiment, the medication administration assembly 5 further contains a mechanism that prevents the accidental administration of medication. In this embodiment, administration of the medication is only possible once the device of the present invention has been correctly placed on the subject at the site where the medication is to be administered. Sites of administration can include, for example a site selected from the group consisting of the subject's arm, the subject's thigh, the subject's shoulder, the subject's hip, and the subject's abdomen.

In certain embodiments where the subject exposes or de-retracts a hypodermic needle, the mechanism can prevent deliver of the medication until the needle is correctly injected or inserted into the correct site on the subject.

An example of a mechanism that prevents the accidental administration of medication suitable for use in the automatic medication injection device of the present invention is disclosed in US Patent Application 20050273054 A1. Another example of a mechanism that prevents the accidental administration of medication suitable for use in the automatic medication injection device of the present invention is disclosed in PCT publication WO/2013/034986 A2. Another example of a mechanism that prevents the accidental administration of medication suitable for use in the automatic medication injection device of the present invention is disclosed in EP2217310A4.

The Activation Assembly.

In one embodiment an activation assembly 7 is attached to the activation end 3 of the flexible tube 1 of the medication injection device of the present invention. The activation assembly 7 contains a mechanism that applies a force that administers the medication. One of ordinary skill in the art can readily select the type of mechanism that may be used in the medication administering device of the present invention. The choice of mechanism may be dictated by several factors, including, for example, the site where a particular medication may be administered to a subject, the volume of medication that may be administered, how the medication is administered, the age of the subject, the species of the subject, the type of medication to be administered, and the like.

The activation assembly 7 may be connected to the activation end 3 of flexible tube 1 of the medication administration device of the present invention by any suitable mechanism. Such mechanisms include, for example, the standardized system of small-scale fluid fittings used for making leak-free connections between a male-taper fitting and its mating female part on medical and laboratory instruments, including hypodermic syringe tips and needles, known as the Luer lock. The activation assembly 7 may be connected to activation end 3 of flexible tube 1 of the medication administration device of the present invention by any mechanism that complies with ISO 594 standards. Alternatively, the activation assembly 7 may be connected to activation end 3 of flexible tube 1 of the medication administration device of the present invention by any mechanism that complies with DIN and EN standards 1707:1996 and 20594-1:1993.

In the embodiment shown in FIG. 6, the activation assembly 7 extends hypodermic needle 17, resulting in insertion of the needle into the subject, and the activation also administers the medication to the subject. In an alternate embodiment, the mechanism administers the medication to the subject only.

In one embodiment, the activation assembly 7 may have a mechanism that prevents the accidental discharge or administration of the medication within the flexible tube, or deployment of the needle, or both the discharge or administration of medication and deployment of the needle. An example of such a mechanism is described in FIG. 6, showing a top that can be moved away, exposing a button.

In one embodiment, the activation assembly 7 is only capable of discharging or administering the medication once the medication administration device of the present invention is correctly situated on the subject in need thereof.

In an alternate embodiment, the activation assembly 7 is only capable of deploying a hypodermic needle once the medication administration device of the present invention is correctly situated on the subject in need thereof.

An example of a mechanism that prevents the accidental administration of medication suitable for use in the automatic medication injection device of the present invention is disclosed in US Patent Application 20050273054 A1. Another example of a mechanism that prevents the accidental administration of medication suitable for use in the automatic medication injection device of the present invention is disclosed in PCT publication WO/2013/034986 A2. Another example of a mechanism that prevents the accidental administration of medication suitable for use in the automatic medication injection device of the present invention is disclosed in EP2217310A4.

An example of a mechanism suitable adaptation for the activation assembly of the medication administration device of the present invention is disclosed in U.S. Pat. No. 5,536,249.

Figure 11:
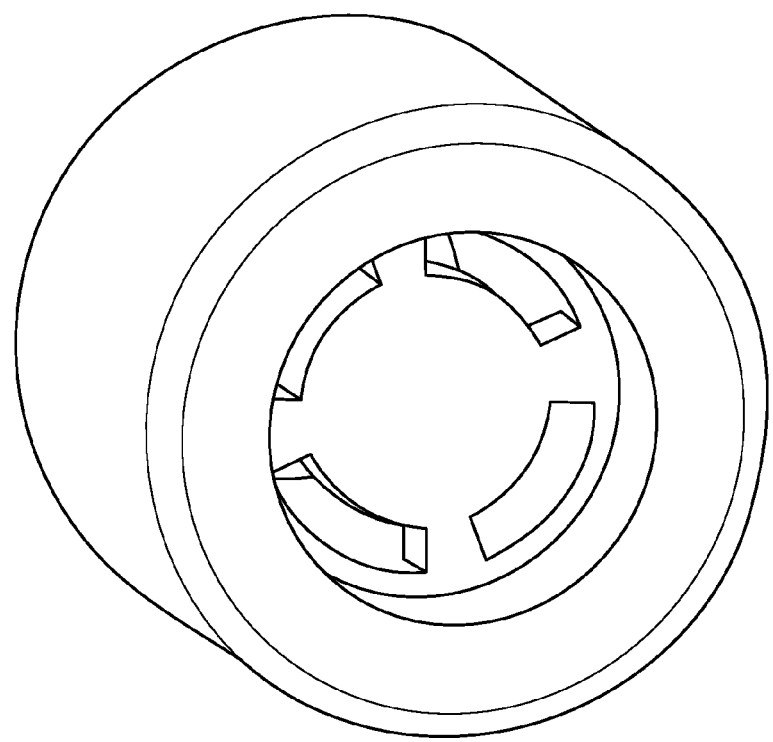
FIG. 11 shows one embodiment of a gas deployment assembly used in one embodiment of the activation assembly of a medication administration device of the present invention.
Figure 12:
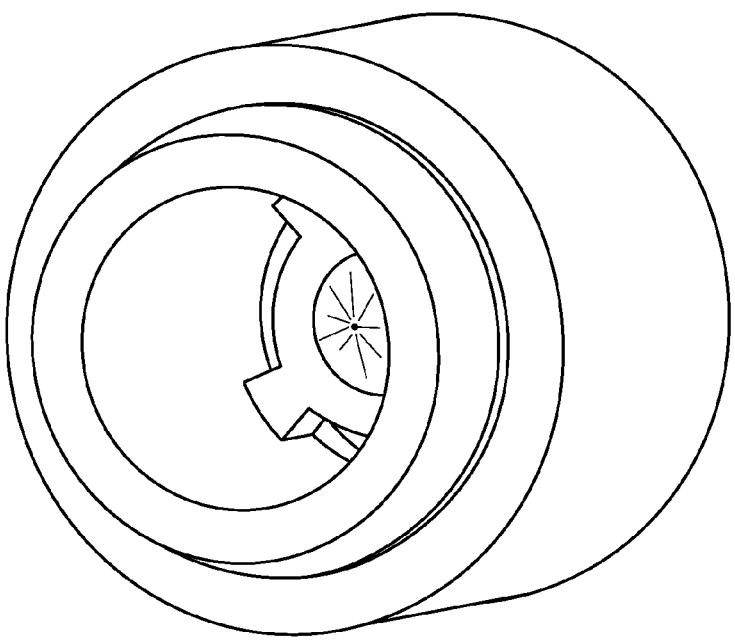
FIG. 12 shows an alternate embodiment of a gas deployment assembly used in one embodiment of the activation assembly of a medication administration device of the present invention.
Figure 13:
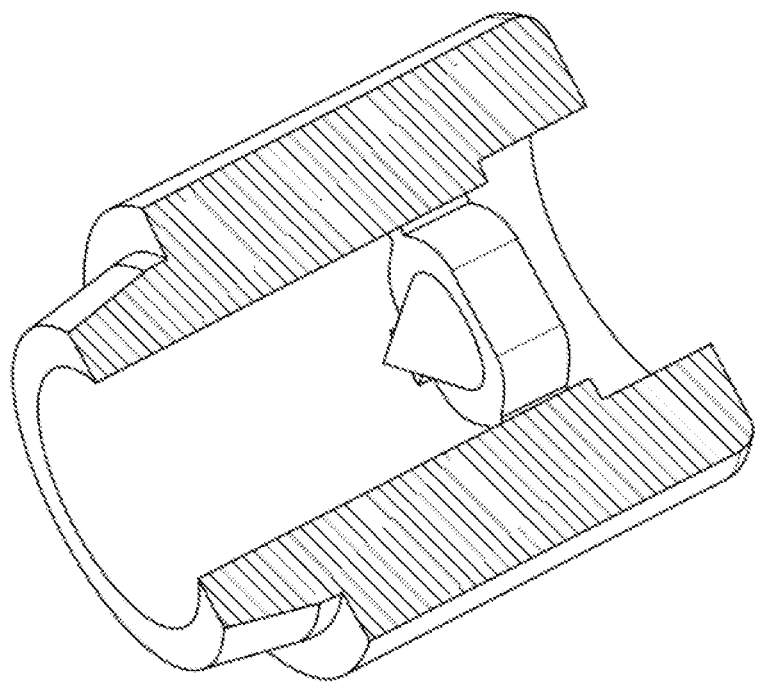
FIG. 13 shows an alternate embodiment of a gas deployment assembly used in one embodiment of the activation assembly of a medication administration device of the present invention.

Referring to FIG. 8, an activation assembly 7 is attached to the activation end 3, and a gas cartridge 19 is located between deployment assembly 8 and activator 9. FIGS. 11 to 13 show several embodiments of deployment assemblies. One of ordinary skill in the art can readily appreciate that gas cartridge 19 can be replaced with a spring, or other means to apply force. For example, FIG. 8 shows an alternative deployment assembly 20 is shown, that contains a mechanism to regulate the amount of medication administered.

Figure 14:
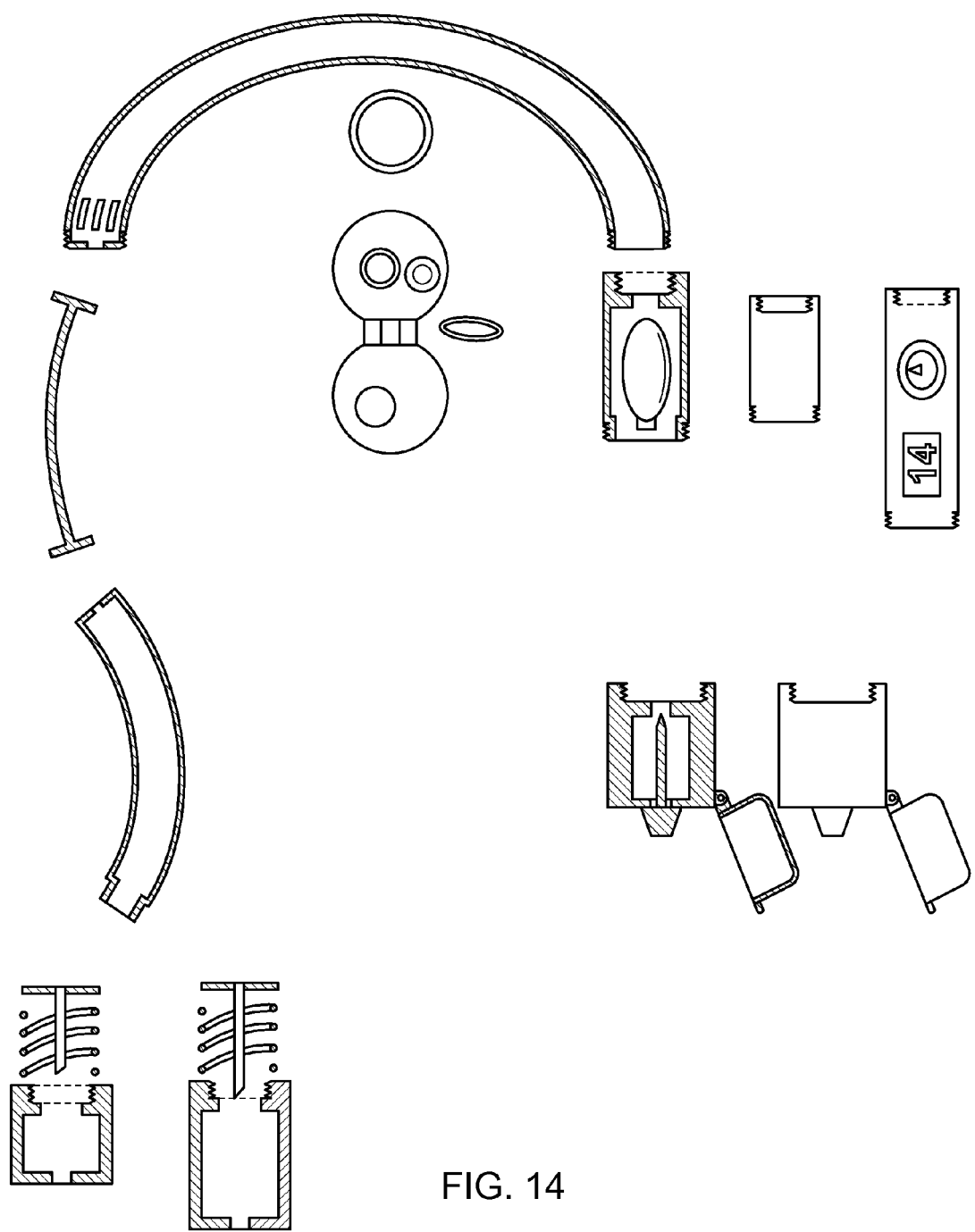
FIG. 14 shows a cut away and exploded view of an alternate embodiment of the medication administration device of the present invention that forms an open bracelet, with the tag shown in FIG. 16 attached. A variety of administration and activation ends are also shown.

FIG. 14 shows a cut away view of a variety of activation and medication administration assemblies.

In one embodiment, the force regulates the dose of medication. Any suitable mechanism to regulate the dose of medication may be used. For example, in the embodiments using a gas cartridge, a valve limiting the amount of propellant released may be used. FIGS. 8 and 14 show an alternative deployment assembly 20 that contains a mechanism to regulate the amount of medication administered.

The Flexible Tube.

In one embodiment, the device comprises a flexible tube 1, having medication administration end 2 and an activation end 3. In certain embodiments, the flexible tube 1 has vents 20 at the medication administration end 2. The vents may be modified to prevent blockage and/or contamination. Flexible tube 1 has a lumen 14 that contains syringe 16, with plunger 15 at the first end of the syringe, and a rupturable seal 18 at the second end 23 of syringe 16. In the embodiment shown, the second end of syringe 16 is immediately adjacent to the medication administration end 2.

In certain embodiments, vents 20 allow gas to escape following activation of the device.

In one embodiment, the syringe 16 may have more than one chamber. For example, syringe 16 may have a first chamber containing lyophilized medication, and a second chamber containing a liquid that can reconstitute the lyophilized medication. In one embodiment, the application of pressure to the plunger 15 first reconstitutes the medication prior to breaking the rupturable seal 18 at the second end 23 of syringe 16.

The flexible tube may be any color and the tube may be opaque or transparent. The flexible tube may be constructed of any material capable of imparting the desired physical properties, such as, for example, strength and flexibility so that the medication administration device of the present invention may be worn by the subject in need thereof without compromising the integrity and/or sterility of the medication contained within the tube.

The flexible tube may be of any length, provided the flexible tube allows a subject in need thereof to wear the medication administration device and the flexible tube contains sufficient medication for the correct administration to the subject.

In one embodiment, the activation and medication administration assemblies are removable, allowing the flexible tube to be replaced by the subject. In an alternate embodiment, the medication administration assembly is replaceable, and the flexible tube may contain sufficient medication for one, or more than one dose.

In one embodiment, the material suitable to manufacture the flexible tube of the medication administration device of the present invention complies with drug regulatory guidelines. In one embodiment, flexible tube 1 may be formed or bent into a bracelet shape by the subject. In one embodiment, flexible tube 1 is capable of maintaining the bracelet shape formed by the subject. In one embodiment, syringe 16 is made from the same material as flexible tube 1. In one embodiment, plunger 15 is made from the same material as flexible tube 1.

Materials suitable to manufacture the flexible tube of the automatic medication injection device of the present invention include PVC, LDPE, polyethylene, and combinations thereof.

In one embodiment, the flexible tube of the medication administration device comprises an inner tube and an outer tube. The inner tube may be made of any suitable material that complies with drug regulatory guidelines. The inner tube may be made from any material capable of imparting the desired physical properties, such as, for example, strength and flexibility so that the medication administration device of the present invention may be worn by the subject in need thereof without compromising the integrity and/or sterility of the medication contained within the tube. The inner tube may be made of materials such as, for example, PVC, LDPE, polyethylene, and combinations thereof.

The outer tube of the flexible tube of the medication administration device may be made from any material capable of imparting the desired physical properties, such as, for example, shape, strength and flexibility, so that the medication administration device of the present invention may be worn by the subject in need thereof without compromising the integrity and/or sterility of the medication contained within the inner tube.

In one embodiment, the outer tube may protect the inner tube.

The outer tube may be constructed in any manner. For example, the outer tube may be a solid tube. Alternatively, the outer tube may be a woven or braided tube. In one embodiment, the subject may choose how the outer tube is constructed.

The outer tube may be any color and texture. In one embodiment, the subject may choose the color and/or texture of the outer tube.

In an alternate embodiment, the outer tube may be personalized by the subject. Personalization may include, for example the subject's name, address, medical condition, medication, or any combination thereof.

In one embodiment, the flexible tube of the medication administration device is a sealed unit containing medication, and the needle is attached to the first end of the flexible tube and the attachment breaks the seal of the flexible tube. In one embodiment, attachment of the needle does not break the seal of the flexible tube, and the seal of the flexible tube is broken immediately prior to the administration of the medication.

In one embodiment, the first and second ends of the flexible tube are inserted into a clasp, thereby forming a bracelet or loop. In one embodiment, the clasp also protects the trigger and/or the needle. Any clasp capable of protecting at least one of the trigger, needle, first and second ends is suitable for use in the automatic medication administration device of the present invention.

One embodiment of a clasp suitable for use in the automatic medication administration device of the present invention is shown in FIG. 1.

Medication.

The device of the present invention may be used to deliver medication to a subject in need thereof. The medication may be required to be administered under an emergency condition. Alternatively, the medication may be required to be administered to treat a disease. In one embodiment, the medication is in liquid form. The medication administration device of the present invention may administer one, or, alternatively, more than one dose of medication.

The medication administration device of the present invention may administer one, or more than one medication to a subject in need thereof.

In one embodiment, the volume of medication that is administered in a dose may be fixed, such that the device of the present invention may deliver one, or more than one dose of medication in a pre-determined volume. Alternatively, the user may select the volume of medication that is administered in a dose.

In one embodiment, a volume of about 0.1 milliliters to about 1 milliliter or more of a medication may be administered in an administration time period of about one second to about twelve hours. In one embodiment, the administration time period for the same range of volumes may range from about one second to about thirty seconds, but is not limited to this range. In certain embodiments, medication volumes of about 0.1 milliliters to about 1 milliliter may be administered in a time duration ranging from about 3 seconds to about 5 seconds. In certain embodiments, medication volumes of about 0.1 milliliters to about 1 milliliter may be administered in time durations of or shorter than about 20 seconds.

Examples of medication suitable for use in the device of the present invention include glucagon, insulin, adrenaline, epinephrine, anti venom, atropine, antidotes to chemical agents, antibodies and the like.

In one embodiment, the medication suitable for use in the device of the present invention is at least one medication selected from the group of medications identified by tradenames consisting of Acthar, Actimmune, Apokyn, Aranesp, Arixtra, Avonex, Betaseron, Bravelle, Butorphanol, Byetta, Calcijex, Calcitonin, Caverject, Cetrotide, Chorionic Gonadotropin, Cimzia, Copaxone, Copegus, DDAVP, D.H.E-45, Delatestryl, Delestrogen, Depo-Estradiol, Depo-Provera 150, Depo-SubQ Provera 104, Depo-Testosterone, Desmopressin, Dihydroergotamine, Edex, Eligard, Enbrel, Epipen, Epogen, Exjade, Faslodex, Fertinex, Follistim, Forteo, Fragmin, Fuzeon, Ganirelix acetate, Genotropin, Gleevec, Glucagon, Gonal, Heparin, Humatrope, Humira, Imitrex, Increlex, Infergen, Innohep, Insulin, Intron A, iPlex, Ketorolac, Kestrone, Kineret, Kuvan, Leukine, Leuprolide Acetate, Lovenox, Lupron, Luveris, Medroxyprogesterone, Menopur, Methotrexate, Miacalcin, Muse, Neumega, Neulasta, Neupogen, Nexavar, Norditropin, Novarel, Nutropin, NuvaRing, Omnitrope, Orfadin, Ovidrel, Pegasys, Peg-Intron, Pregnyl, Procrit, Profasi, Progesterone, Pulmozyme, Raptiva, Rebetol, Rebif, Repronex, Revlimid, Ribasphere, Ribavirin, Saizen, Sandostatin, Sensipar, Serostim, Somatuline, Sprycel, Somavert, Stadol, Sumatriptan, Supprelin, Sutent, Symlin, Tarceva, Testosterone, Temodar, Tev-Tropin, Thalomid, Tobi, Tykerb, Vitamin B12, Vitamin K, Xeloda, Zemplar, and Zorbtive.

Use of the Device of the Present Invention.

Figure 15:
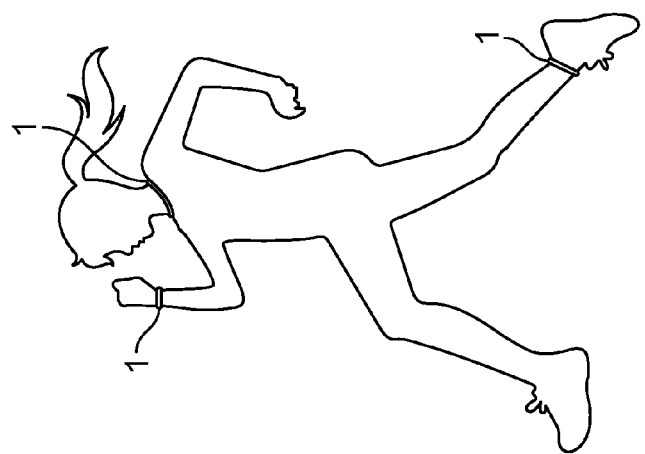
FIG. 15 shows examples of sites where a subject may wear the administration device of the present invention.
Figure 15:
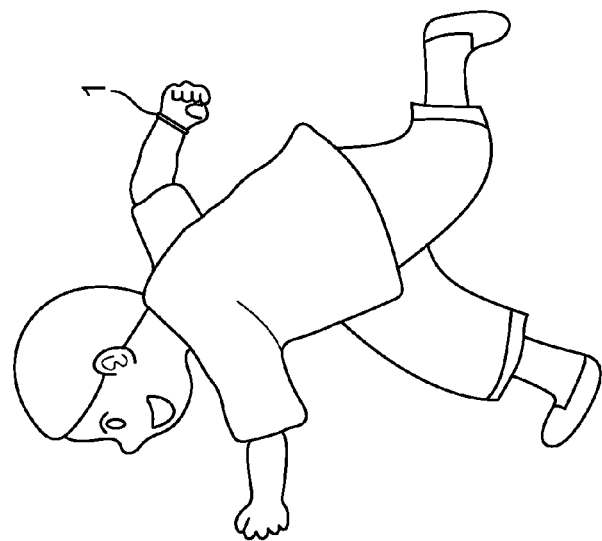
Figure 15:
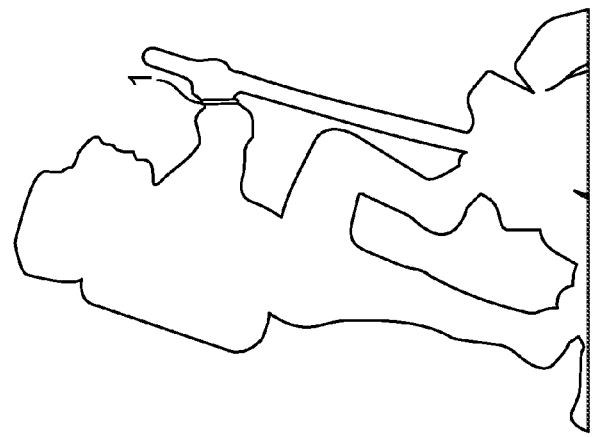
Figure 16:
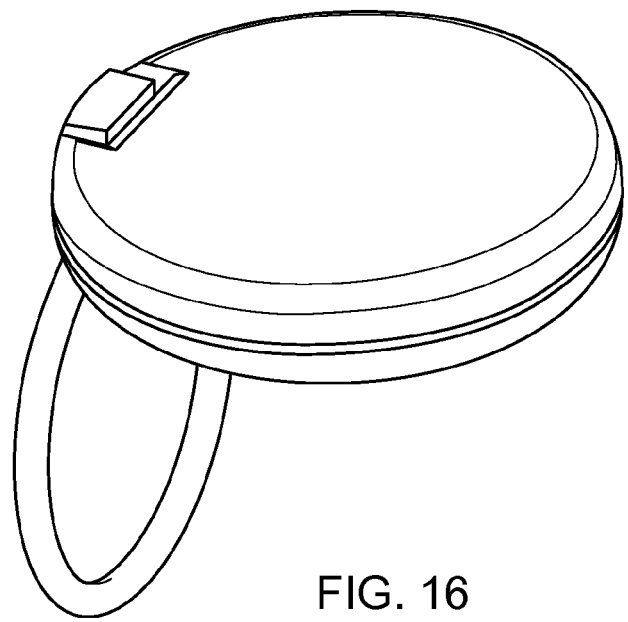
FIG. 16 shows one embodiment of a tag that may be attached to a medication administration device of the present invention. The tag is shown in a closed configuration.
Figure 17:
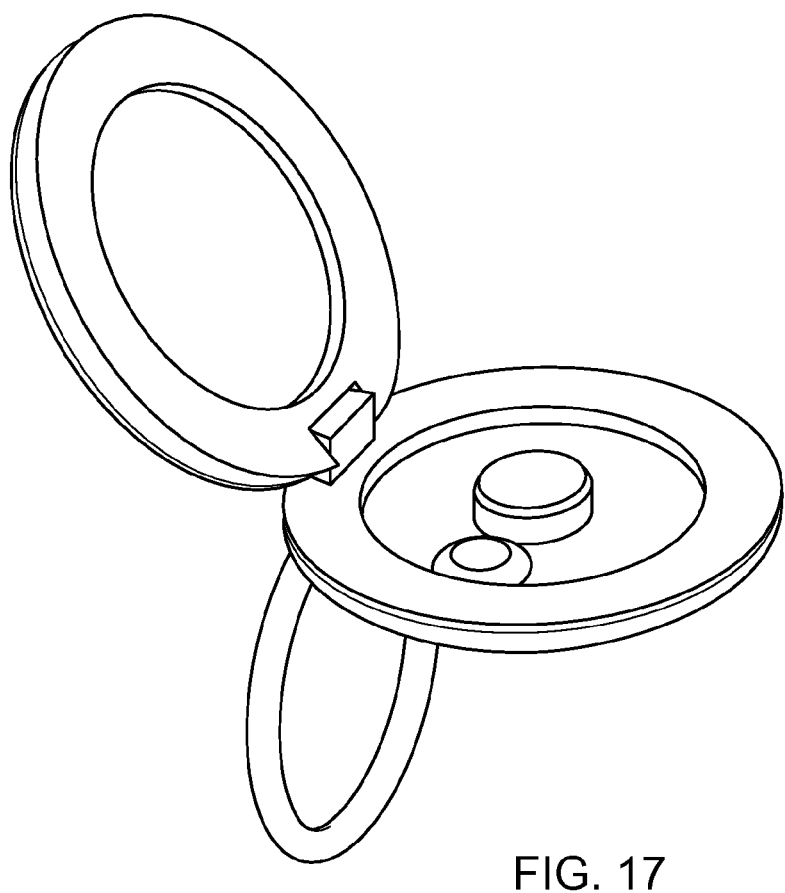
FIG. 17 shows the tag of FIG. 5 in an open configuration.
Figure 19:
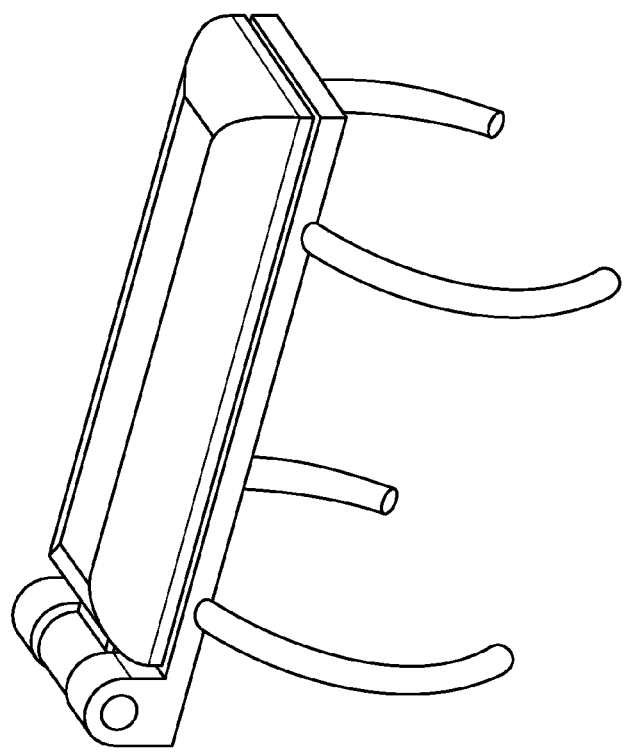
FIG. 19 shows the tag of FIG. 7 in an open configuration.
Figure 18:
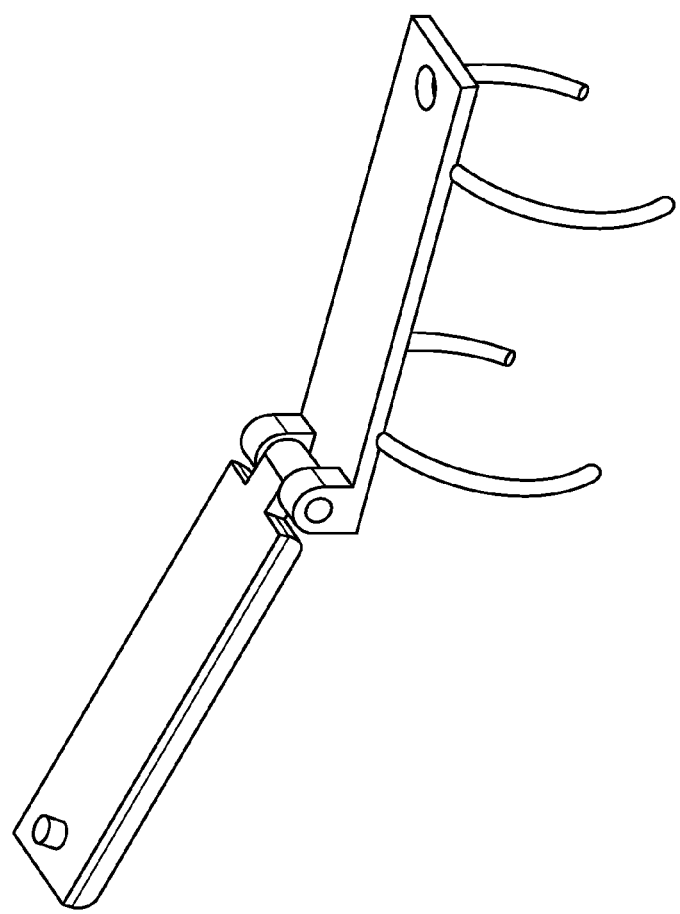
FIG. 18 shows another embodiment of a tag that may be attached to a medication administration device of the present invention. The tag is shown in a closed configuration.

The medication administration device can be worn on a subject's person. In one embodiment, the medication administration device may be worn on the subject's wrist. Alternatively, the medication administration device may be worn on the subject's arm. Alternatively, the medication administration device may be worn on the subject's leg. Alternatively, the medication administration device may be worn around the subject's neck. Alternatively, the medication administration device may be attached to the subject's clothing, or on an item worn or carried by the subject. Examples of sites where the medication administration device of the present invention may be worn or attached are shown in FIG. 15.

In one embodiment, the medication administration device of the present invention is formed into a closed bracelet or loop by inserting the activation end and the medication administration end into a clasp.

In an alternate embodiment, the medication administration device of the present invention is formed into an open bracelet or loop by bending the medication administration device around the site where the subject desires to wear or attach the medication administration device.

In one embodiment, the medication administration device may be worn during any and all physical activities that a subject may perform. In one embodiment, the medication administration device of the present invention is waterproof.

In one embodiment, the medication administration device of the present invention may be further configured to identify the medication contained within the device. In one embodiment, the medication administration device of the present invention may be further configured to identify the medical condition that a subject may have. In one embodiment, the medical condition, or the medication, or combinations thereof, are identified by pendants or tags. The tags can be removably attached to the flexible tube. In one embodiment, pendants suitable for use in the present invention are the identification pendants offered by organizations such as the MedicAlert Foundation.

In one embodiment, the pendant or tag may contain information that identifies the subject and provides instructions to administer the medication. The information can be written. Alternatively, the information can be pictorial. In one embodiment, the information is audible. In the embodiments where the information is audible, the tag or pendant contains a speaker. In certain embodiments, the audible information is customizable. For example, the instructions to use the device of the present invention may be transmitted to the subject in the voice of someone familiar to the subject. Examples of tags or pendants that contain audible information are shown in FIGS. 16 to 19. In these examples, the tag is opened to display or receive the information.

The medication administration device of the present invention may be used by a subject in need thereof. Alternatively, the medical administration device of the present invention may be used on a subject in need thereof. The subject in need thereof may be any species or age. In one embodiment, the subject in need thereof is human.

The medication administration device of the present invention may be used to administer medication at any site on a subject in need thereof. By way of example, and not intending to limit the present invention, the medication administration device of the present invention may be capable of administering medication at any site, including, for example, the subject's arm, or the subject's thigh, or the subject's hip, or the subject's shoulder, or the subject's abdomen. Alternatively, the medication administration device of the present invention administers medication at a specific single site on a subject in need thereof. In one embodiment, the medication administration device of the present invention administers medication at a single site in a subject in need thereof, wherein the site is selected from the group consisting of the subject's arm, the subject's thigh, the subject's hip, the subject's shoulder, and the subject's abdomen. The medication administration device of the present invention may be specifically configured to administer medication at the selected single site. Examples of the configuration may include a particular hypodermic needle length.

In one embodiment, the medication administration device of the present invention administers medication in a subject's shoulder.

In one embodiment, the medication administration device of the present invention administers medication in a subject's deltoid muscle.

In one embodiment, the medication administration device of the present invention administers the medication to the subject via at least one route of administration selected from the group consisting of an intravenous route of administration, a subcutaneous route of administration, and an intramuscular route of administration.

In one embodiment, the automatic medication administration device of the present invention administers the medication to the subject via a route of administration selected from the group consisting of an intravenous route of administration, a subcutaneous route of administration, and an intramuscular route of administration.

Activation of the Medication Administration Device of the Present Invention:

In one embodiment, the medication administration device of the present invention may be operated like a conventional syringe, in that the subject manually de-retracts or exposes a hypodermic needle, injects or inserts the needle into the subject's body at the desired site of administration, and administers the medication.

Alternatively, the medication administration device of the present invention administers medication automatically to the subject, following activation of the device. In one embodiment, the automatic or mechanical steps are triggered or initiated by the subject placing the injection device of the present invention at the desired site of administration.

Using the device described in FIG. 6 as an example, and without intending to be limited thereby, depression of button 13 activates the device, releasing a force, and the force is transmitted from the deployment assembly 8 into the lumen 14 of flexible tube 1. In the embodiment shown, the force is provided by button 13 causing gas cartridge 19 to release some, or all of its contents (see FIG. 8). The force presses against plunger 15, and causes the second end of syringe 16 to rupture. The rupture of the second end enables medication to move into administration assembly 7. In the embodiment shown, the rupture of the second end of syringe 16 also de-retracts hypodermic needle 17 and rupture of sealed end 6.

In one embodiment, the device of the present invention delivers medication to the subject by:
a. the subject placing the medication administration end of the device on a site where medication administration is desired;
b. generating a force;
c. the force moving the plunger from the activation end toward the medication administration end of the flexible tube;

d. the movement of the plunger rupturing the rupturable seal located at the second end of the syringe and causing the medication to flow out from second end of the syringe through medication administration end of the flexible tube into the medication administration assembly; and e. the flow of the medication into the medication administration assembly rupturing the seal of the medication administration end, thereby administering the medication to the subject.

In one embodiment, the activation assembly generates the force. In a further embodiment, the force is generated using a compressed gas capsule or cylinder. In a further embodiment, the force is generated using a spring.

In one embodiment, the medication administration assembly is a hypodermic needle contained within the activation assembly, and the flow of the medication into the medication administration assembly inserts the hypodermic needle in the subject and ruptures the seal of the medication administration end, thereby administering the medication to the subject.

The subject may decide the volume or dose of the medication to be administered, and in this embodiment, the device of the present invention administers a volume of medication that is set by the subject. Alternatively, the device of the present invention administers a fixed, predetermined volume or dose of medication.

The subject may select the route of administration. In this embodiment, the subject may select the degree or depth at which a hypodermic needle is inserted or injected into the subject. Alternatively, in the case where medication is administered without the use of a hypodermic needle, such as, for example, a viscous liquid administrator, the subject may select the force and/or volume of the mediation that is administered.

Alternatively, the route of administration is not determined by the subject. In this embodiment, the degree or depth at which the hypodermic needle is inserted into the subject (or, as in the case of a viscous liquid administrator, the subject may select the force and/or volume of the mediation that is administered) is pre-determined, such as, for example, to enable administration of medication at a pre-determined delivery site, route of administration, subject, or combinations thereof. In one embodiment, the trigger deploys the needle to a predetermined degree or depth.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A wearable device for administering medication to a subject, comprising:
   a flexible tube comprising a medication administration end and an activation end, the flexible tube defining a lumen between the medication administration end and the activation end;
   a medication administration assembly attached to the medication administration end,
      wherein the medication administration assembly comprises a needle in fluid communication with the medication administration end, wherein the needle has
         a first position where the needle is retracted within the medication administration assembly; and
         a second position where the needle extends out of the medication administration assembly, thereby allowing insertion of the needle into the subject to administer the medication to the subject,
      wherein the medication administration further comprises a secondary rupturable seal provided to an end of the medication administration assembly, said end being distal to the medication administration end of the flexible tube, wherein the needle punctures the second rupturable seal when the needle is at the second position,
      wherein the needle is spring-biased within the medication administration assembly when the needle is at the first position;
   an activation assembly attached to the activation end,
      wherein the activation assembly comprises:
         a force generator for generating a force to move the plunger within the lumen, in a direction from the activation end to the medication administration end of the flexible tube; and
         an activator operatively connected to the force generator to control the force generator,
      wherein the force generator is either a cartridge containing pressurized fluid, or a spring,
      wherein the activator comprises a button for controlling the release of the pressurized fluid into the lumen, when the force generator is a cartridge containing pressurized fluid;
   a syringe disposed within the lumen, wherein the syringe contains the medication and comprises a first end and an opposite second end;
   a plunger disposed within the lumen and operatively connected to the first end of the syringe; and
   a rupturable seal provided to the second end of the syringe, the second end of the syringe being approximate to the medication administration end,
   wherein the activation assembly is configured to activate the plunger and break the rupturable seal, such that a fluid communication is established between the second end of the syringe and the medication administration assembly to allow transportation of the medication from the syringe to the medication administration assembly through the medication administration end.

2. The device of claim 1, wherein the medication administration end and the activation end of the flexible tube are configured to operatively approach each other to form a partial loop of the flexible tube.

3. The device of claim 2, further comprising a cover member, into which the medication administration end and the activation end of the flexible tube, the medication administration assembly, and the activation assembly are received to form a closed loop.

4. The device of claim 1, wherein the needle moves to the second position upon the activation of the plunger and the breakage of the rupturable seal.

5. The device of claim 1, wherein the plunger forms an airtight seal within the syringe, such that when the plunger is activated by the activation assembly, a pressure is applied to the medication within the syringe by the plunger, the pressure being sufficient to break the rupturable seal.

6. The device of claim 1, further comprising a cap for covering the button, the cap being pivotably mounted to the activator through a hinge.

7. The device of claim 1, further comprising at least one vent provided to the flexible tube, through which the pressurized fluid is released from the lumen.

8. The device of claim 1, wherein the plunger forms an airtight seal within the lumen.

9. The device of claim 1, further comprising at least one tag removably attached to the flexible tube, the tag being representative of information related to at least one of a medical condition of the subject and the medication.

* * * * *